Figure 1:
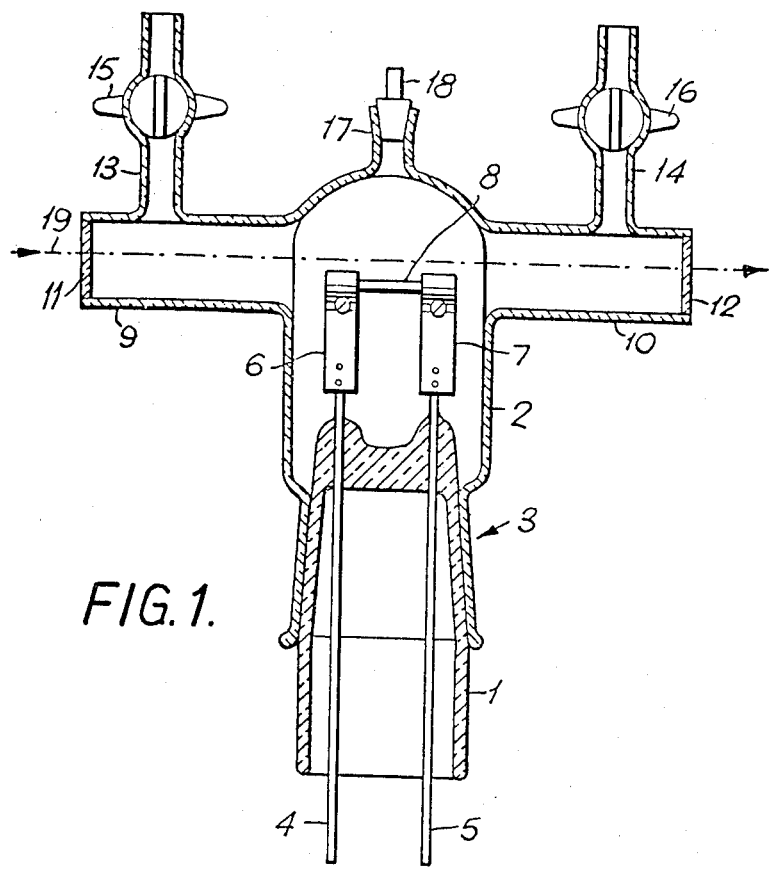

United States Patent [19]

West

[11] 3,947,125

[45]* Mar. 30, 1976

[54] ATOMIC ABSORPTION AND FLUORESCENCE SPECTROSCOPY

[75] Inventor: Thomas Summers West, Croydon, England

[73] Assignee: National Research Development Corporation, London, England

[ * ] Notice: The portion of the term of this patent subsequent to Jan. 7, 1992, has been disclaimed.

[22] Filed: Oct. 10, 1974

[21] Appl. No.: 513,567

Related U.S. Application Data

[62] Division of Ser. No. 2,532, Jan. 13, 1970, Pat. No. 3,858,980.

[30] Foreign Application Priority Data

Jan. 16, 1969 United Kingdom.............. 2590/69

[52] U.S. Cl. .................. 356/85; 250/301; 250/373
[51] Int. Cl.² ........................................ G01J 3/30
[58] Field of Search ............... 250/301, 373; 356/85

[56] References Cited

UNITED STATES PATENTS

| | | | |
|---|---|---|---|
| 3,503,686 | 3/1970 | Walsh et al. | 356/85 |
| 3,581,085 | 5/1971 | Barrett | 250/301 |

Primary Examiner—Archie R. Borchelt
Attorney, Agent, or Firm—Cushman, Darby & Cushman

[57] ABSTRACT

In analysing a sample by atomic absorption or atomic fluorescence spectroscopy, the cloud of free atoms which interact with incident radiation is produced by heating a graphite body, disposed below the interaction region, on which the sample has been deposited. The body is heated in an inert atmosphere by passing electric current through it. Compact forms of apparatus which may replace the burner system of a conventional spectrometer utilise a horizontally disposed graphite rod around which flows a stream of inert gas.

10 Claims, 4 Drawing Figures

ATOMIC ABSORPTION AND FLUORESCENCE SPECTROSCOPY

This is a division, of application Ser. No. 2,532 filed Jan. 13, 1970, now U.S. Pat. No. 3,858,980.

In the techniques of atomic absorption and atomic fluorescence spectroscopy, as used for the analytical determination of various elements, a cloud of free atoms in the vapour phase is produced from a sample under investigation and radiation of an appropriate wavelength to interact with the atoms is caused to impinge on this cloud, measurements being made either of the proportion of the incident radiation which is transmitted through the cloud or of the intensity of the fluorescent radiation emitted from the cloud as a result of excitation by the incident radiation.

Various means are known whereby the cloud of free atoms may be produced, but the one most commonly used, particularly in commercially available apparatus, involves spraying of a solution of the sample into a flame. This method is, however, very inefficient and is subject to the usual risks involved in the use of flames.

It is an object of the present invention to provide a relatively simple means, which avoids the disadvantages involved in the use of a flame, for producing free atoms from a sample under investigation by atomic absorption or atomic fluorescence spectroscopy.

According to the invention, in a method of atomic absorption or atomic fluorescence spectroscopy the cloud of free atoms which interacts with incident radiation is produced from a sample under investigation by heating a graphite body on which the sample has been deposited, so as to evaporate the sample, the body being disposed wholly below the region in which the interaction occurs and being heated by the passage through it of an electric current while it is surrounded by an inert atmosphere.

The graphite body may suitably be in the form of a slender rod disposed with its axis horizontal. The body may be disposed in a chamber through which a stream of inert gas is caused to flow, the chamber being provided with optical windows for the passage of radiation into and out of the chamber; alternatively the body may be arranged so that it is normally exposed to the ambient atmosphere, a curtain of inert gas being projected around the body when it is heated so as to shield it from the ambient atmosphere.

Apparatus for use in a method according to the invention may comprise a slender rod of graphite the ends of which are releasably secured to terminals via which an electric current may be passed through the rod, and means enabling an inert atmosphere to be maintained around the rod, the arrangement being such that with the apparatus disposed so that the axis of the rod is horizontal a sample to be investigated may be deposited on the rod, radiation from an external source may be directed horizontally into a region just above the rod, and radiation emerging horizontally from said region may be detected by an external detector.

Figure 2:
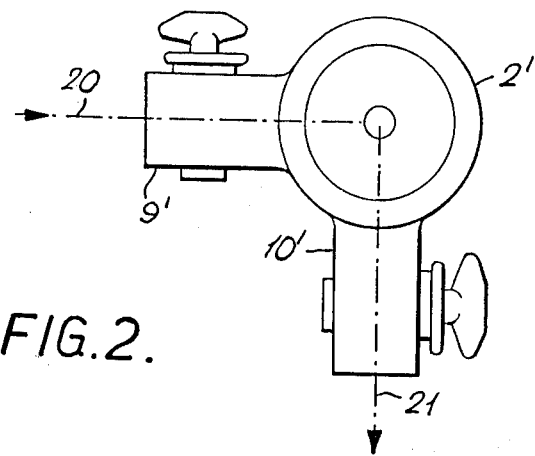
Figure 3:
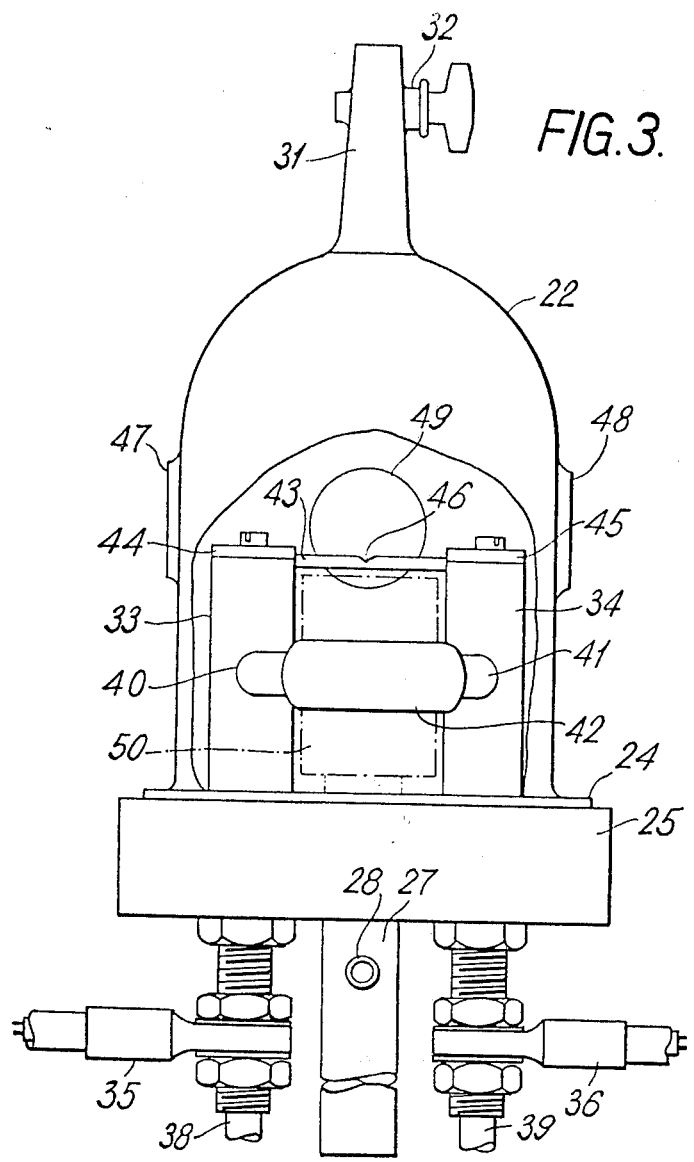
Figure 4:
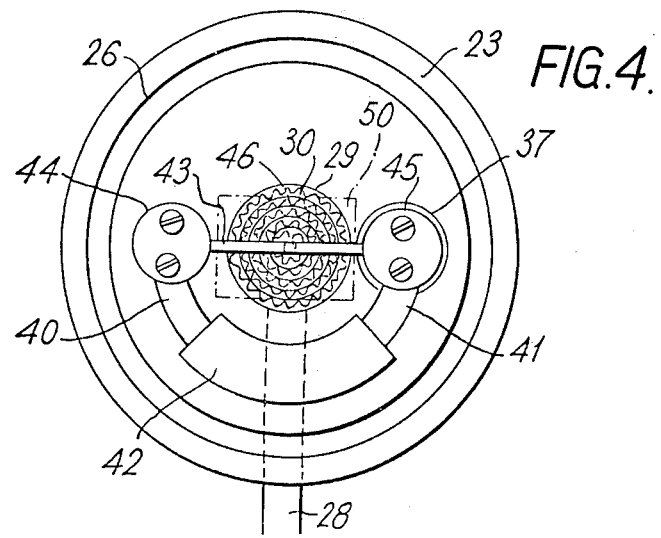

Thus in performing the invention use may be made of arrangements such as are illustrated in the accompanying drawings, in which:

FIG. 1 is a sectional side elevation of an apparatus suitable for use in atomic absorption spectroscopy, FIG. 2 is an underneath plan view of part of an apparatus generally similar to that shown in FIG. 1, but modified for use in atomic fluorescence spectroscopy, FIG. 3 is a side elevation, partly cut away to show internal details of an alternative apparatus suitable for use in either atomic absorption or atomic fluorescence spectroscopy, and FIG. 4 is a plan view of part of the apparatus shown in FIG. 3.

Referring to FIG. 1, the apparatus shown therein comprises a chamber of borosilicate glass made in two parts, a base 1 and a cover 2, these parts mating by means of a cone joint 3 which in use is sealed with grease to make the chamber gas-tight. The base 1 has sealed through it two tungsten rods 4 and 5 to the ends of which inside the chamber are respectively secured two stainless steel terminals 6 and 7. In the terminals 6 and 7 are releasably clamped the ends of a rod 8 of spectrographically pure graphite, such as is obtainable from Morganite Ltd.; the rod 8 may suitably have a diameter of one to two millimeters, the length of the rod 8 between the terminals 6 and 7 being about two centimeters.

The main part of the cover 2 is of cylindrical form, having a length of about nine centimeters and a diameter of about six centimeters, and this part has sealed to it two coaxial side arms 9 and 10 the free ends of which respectively have sealed across them windows 11 and 12 of optical quality silica. The side arms 9 and 10 respectively communicate with tubes 13 and 14, respectively provided with taps 15 and 16, via which a stream of inert gas may be passed through the chamber. The cover 2 also has sealed to it an inlet tube 17, normally closed by a stopper 18, which is disposed so that samples may be introduced through it and deposited on the rod 8. In use the parts 1 and 2 are fitted together so that the axes of the side arms 9 and 10 are parallel to the axis of the rod 8 and lie slightly above the terminals 6 and 7.

The apparatus shown in FIG. 1 is intended for use in a conventional atomic absorption spectrometer in place of the usual burner-nebulizer system, being disposed in the instrument between the detection system and a suitable light source so that a beam of radiation (indicated by the line 19 in FIG. 1) from the light source passes through the chamber, via the windows 11 and 12, to the detection system; the beam 19 is directed parallel to the axes of the side arms 9 and 10 and passes just above the rod 8, which thus occupies approximately the same position as would the primary cone of the flame produced by a conventional burner. The rod 8 is arranged to be heated by passing through it, via the rods 4 and 5, an electric current which may suitably be derived from a mains supply via a stepdown transformer having a relatively low output voltage (say 6 – 8 volts). The temperature to which the rod 8 is heated will depend upon the particular element which is to be analysed; it can of course be determined by choice of the diameter of the rod 8 and the magnitude of the current, and can be readily monitored by means of an optical pyrometer. Typically the temperature may be in the range 2000° – 2500°C, in which case a current of the order of 100 amperes will be required when using a rod 8 of the dimensions indicated above.

In operation, a sample to be investigated as deposited on the rod 8, in the form of an aqueous solution, by means of a micrometer syringe introduced through the tube 17, the rod 8 having previously been heated by passing current through it and then allowed to cool to a temperature of the order of 100°C. After a period sufficient to allow the water to evaporate, the rod 8 is again heated by passing current through it for about five seconds, so as to volatilise the sample and produce a cloud of free atoms which rises into the path of the beam 19 above the rod 8, and a measurement is made of the intensity of the light transmitted through the chamber; this is of course a comparative measurement with reference to the intensity of the light transmitted through the chamber when the rod 8 is unheated.

In order to avoid oxidation of the rod 8 it is necessary to maintain an inert atmosphere in the chamber during operation, preferably by arranging for a stable flow of an inert gas to occur through the chamber. This ensures that the water which evaporates initially from the rod 8 is swept out of the chamber before atomisation of the sample occurs, and the sensitivity of the instrument can be enhanced by choosing the flow rate so as to increase the rate of diffusion of atomic vapour away from the heated rod 8 without at the same time unduly increasing the rate at which the vapour is swept out of the chamber. In practice satisfactory results have been achieved by using a flow of argon or nitrogen, at a pressure slightly above atmospheric, with a flow rate of a few liters per minute.

With the arrangement described above, it is possible to make investigations on a series of samples at intervals of about two minutes (sufficient to allow the rod 8 to cool to an appropriate temperature) without encountering any "memory" effects, since the rod 8 is effectively self-purging when heated. Before making such a series of investigations it is of course desirable to ensure that any initial contamination of the rod 8 is removed by heating it for a sufficient period with the inert gas flowing. A rod 8 having the dimensions indicated above can normally be used for many individual analyses before needing to be replaced; when necessary, replacement of the rod 8 can be readily effected.

The base 1 with the rod 8 mounted on it may be used in conjunction with a modified form of cover to constitute an apparatus generally similar to that shown in FIG. 1 but suitable for use in atomic fluorescence spectroscopy. As shown in FIG. 2, the cover 2' in this case is generally similar to the cover 2 but has side arms 9' and 10' disposed with their axes at right angles in place of the side arms 9 and 10, the axes of the side arms 9' and 10' being disposed at a level corresponding to that of the axes of the side arms 9 and 10. In this case, in use a beam of radiation (indicated by the line 20 in FIG. 2) enters the chamber through the side arm 9' so as to interact with a cloud of free atoms produced above the rod 8, and the detection system is arranged to respond to fluorescent radiation emitted by the cloud and emerging from the chamber through the side arm 10' (as indicated by the line 21 in FIG. 2).

Referring now to FIGS. 3 and 4, the apparatus shown therein is basically similar to, but rather more compact than, the apparatus shown in FIG. 1 and is intended for use in a similar manner. In this case, the apparatus comprises a chamber incorporating a borosilicate glass dome 22 having dimensions similar to those of the main part of the cover 2, and a metal base plate 23, the dome 22 having sealed to its mouth a metal flange 24 which is held against the base plate 23 by means of a removable metal clamping ring 25, the joint between the flange 24 and the base plate 23 being sealed by means of a rubber ring 26 disposed in a circular groove in the base plate 23. The base plate 23 is secured to a metal pillar 27 which may be held in a clamp mounted on an optical bar, the upper end of the pillar 27 being hollow and the space within it connecting with a supply tube 28 for inert gas and a circular aperture 29 formed in the base plate 23. Within the aperture 29 is disposed a series of concentric rings of metal foil 30 which are alternately crimped and plain so as to provide a multiplicity of inlet passages for producing a laminar flow of inert gas into the chamber. The dome 22 has formed at its upper end a gas outlet tube 31 provided with a tap 32.

Extending through the base plate 23 are two stainless steel terminal posts 33 and 34 respectively connected to external leads 35 and 36 respectively, the terminal post 33 being in contact with the base plate 23 and the terminal post 34 being electrically insulated from the base plate 23 by means of insulating bushes such as 37. The terminal posts 33 and 34 are hollow, their upper ends being closed, and in use of the apparatus are arranged to be cooled by circulating water through them by means of inlet and outlet tubes 38 and 39, the interiors of the terminal posts 33 and 34 being connected together by side tubes 40 and 41 and a length of rubber tube 42.

Connected between the terminal posts 33 and 34 is a graphite rod 43 similar to the rod 8, each end of the rod 43 being clamped between the upper end of one of the terminal posts 33 and 34 and a corresponding detachable stainless steel plate 44 or 45. The rod 43 has a small notch 46 formed in it half-way along its length, the notch 46 assisting in accurate location when a sample to be analysed is deposited upon the rod 43. The dome 22 is provided with three windows 47, 48 and 49, similar to the windows 11 and 12, whose centres are disposed somewhat above the rod 43, the windows 47 and 48 being disposed perpendicular to the axis of the rod 43 and the window 49 being disposed parallel to the axis of the rod 43.

As indicated above, the apparatus shown in FIGS. 3 and 4 is used in a similar manner to that shown in FIG. 1, the radiation passing through the windows 47 and 48 in the case of atomic absorption spectroscopy and passing through one of these windows and the window 49 in the case of atomic fluorescence spectroscopy. Since in this case no provision is made for the introduction of a sample while the dome 22 is in position, the dome 22 must, of course, be removed to allow a sample to be deposited on the rod 43 and then replaced before a measurement is made. The provision of the forced cooling of the terminal posts 33 and 34 has two advantages. Firstly, it enables more reproducible results to be obtained, by substantially eliminating any tendency for the contact resistance at the ends of the rod 43 to vary as the rod 43 is heated; secondly it shortens the intervals at which it is possible to make investigations on a series of samples, say to a length of about one minute.

In certain cases, particularly when using very intense radiation sources, it may be found that the presence of the dome 22 gives rise to difficulties due to unwanted reflections. In such cases it is possible to operate the apparatus with the dome 22 removed, provided that precautions are taken to ensure that the rod 43 is shielded from the ambient atmosphere by a curtain of inert gas when it is heated. This may readily be achieved by providing an extension of the gas inlet almost up to the level of the rod 43. For example, the foil 30 may be removed from the aperture 29 and replaced by a tube connecting the aperture 29 to the interior of a rectangular metal box (indicated by the chain line 50, FIGS. 3 and 4) occupying most of the space between the terminal posts 33 and 34, the upper end of this box being filled with foil arranged similarly to the foil 30.

It will be appreciated that the apparatuses described above are relatively simple, compact and safe in operation. By using them in the manner described, it is possible to achieve very high atomisation efficiencies while avoiding any complications due to background effects such as are encountered with flames. It is thus possible to detect very small amounts of individual elements; for example, in the case of atomic absorption spectroscopy it has been found possible to determine silver and magnesium at levels of the order of $10^{-9}$ gram, while in the case of atomic fluorescence spectroscopy it has been found possible to determine silver at a level of the order of $10^{-10}$ gram, magnesium at a level of the order of $10^{-10}$ gram, and cadmium at a level of about $3 \times 10^{-13}$ gram.

I claim:

1. A method of spectroscopy comprising the operations of producing from a sample under investigation a cloud of free atoms in the vapour phase, directing into the cloud radiation of an appropriate wavelength to interact with the atoms, and measuring the intensity of radiation emerging from the cloud, wherein the improvement comprises producing the cloud of free atoms by heating a body of graphite on which the sample has been deposited without moving the graphite body between deposition of the sample and heating of the body, so as to evaporate the sample, the body being disposed wholly below the region in which interaction occurs between the atoms and the radiation directed into the cloud and the body being heated by the passage through it of an electric current while it is surrounded by an inert atmosphere.

2. A method according to claim 1, in which the inert atmosphere is provided by causing a stream of inert gas to flow around the body.

3. A method according to claim 2, in which the body is disposed in a chamber through which a stream of inert gas is caused to flow, the chamber being provided with a first optical window for the passage into the chamber of the radiation directed into the cloud and a second optical window for the passage out of the chamber of the radiation emerging from the cloud.

4. A method according to claim 2, in which the body is arranged so that it is normally exposed to the ambient atmosphere, a curtain of inert gas being projected around the body when it is heated so as to shield it from the ambient atmosphere.

5. A method according to claim 1, in which the graphite body is in the form of a slender rod disposed with its axis horizontal.

6. A method of spectroscopy comprising the operations of producing from a sample under investigation a cloud of free atoms in the vapour phase, directing into the cloud radiation of an appropriate wavelength to interact with the atoms, and measuring the intensity of fluorescent radiation emitted from the cloud as a result of excitation by the radiation directed into the cloud, the measured flourescent radiation travelling from the cloud in a direction different from the direction of the radiation directed into the cloud, wherein the improvement comprises producing the cloud of free atoms by heating a body of graphite on which the sample has been deposited, so as to evaporate the sample, the body being disposed wholly below the region in which interaction occurs between the atoms and the radiation directed into the cloud and the body being heated by the passage through it of an electric current while it is surrounded by an inert atmosphere.

7. A method according to claim 6, in which the inert atmosphere is provided by causing a stream of inert gas to flow around the body.

8. A method according to claim 7, in which the body is arranged so that it is normally exposed to the ambient atmosphere, a curtain of inert gas being projected around the body when it is heated so as to shield it from the ambient atmosphere.

9. A method according to claim 6, in which the graphite body is in the form of a slender rod disposed with its axis horizontal.

10. A method according to claim 6, in which the graphite body is not moved between the deposition on it of the sample and the heating of the body to evaporate the sample.

* * * * *